United States Patent
Cox et al.

(10) Patent No.: US 6,284,941 B1
(45) Date of Patent: Sep. 4, 2001

(54) BANDAGE HAVING A SCAR TREATMENT PAD FOR SCAR MANAGEMENT AND SCAR REPAIR

(76) Inventors: Craig M. Cox, R.D. 4, Box 271, Greensburg, PA (US) 15601; Christopher D. Cox, 137 Whitetail Dr., Harrison City, PA (US) 15636; Perry A. Isenberg, R.D. 4, Box 271, Greensburg, PA (US) 15601

(*) Notice: Subject to any disclaimer, the term of this patent is extended or adjusted under 35 U.S.C. 154(b) by 0 days.

(21) Appl. No.: 09/309,631

(22) Filed: May 11, 1999

Related U.S. Application Data

(60) Provisional application No. 60/123,476, filed on Mar. 9, 1999.

(51) Int. Cl.$^7$ ..................................................... A61F 13/00
(52) U.S. Cl. ............................... 602/48; 602/41; 602/42; 602/43; 602/54
(58) Field of Search .................................. 128/888, 889; 602/41–59

(56) References Cited

U.S. PATENT DOCUMENTS

| | | | |
|---|---|---|---|
| 3,888,247 | * 6/1975 | Stenvall | 602/54 X |
| 3,903,882 | 9/1975 | Augurt | 128/155 |
| 4,226,232 | 10/1980 | Spence | 128/156 |
| 4,460,371 | 7/1984 | Abber | 604/897 |
| 4,925,671 | 5/1990 | Abber | 424/448 |
| 4,991,574 | 2/1991 | Pocknell | 128/156 |
| 5,120,322 | 6/1992 | Davis et al. | 604/265 |
| 5,167,649 | 12/1992 | Zook | 604/307 |
| 5,232,702 | 8/1993 | Pfister et al. | 424/448 |
| 5,330,452 | 7/1994 | Zook | 604/307 |
| 5,415,866 | 5/1995 | Zook | 424/448 |
| 5,423,736 | 6/1995 | Cartmell et al. | 602/42 |
| 5,641,507 | 6/1997 | Devillez | 424/443 |
| 5,662,925 | 9/1997 | Ebert et al. | 429/447 |
| 5,759,560 | 6/1998 | Dillon | 424/402 |
| 5,820,876 | 10/1998 | Hoffmann | 424/449 |

* cited by examiner

Primary Examiner—Kim M. Lewis
(74) Attorney, Agent, or Firm—Webb Ziesenheim Logsdon Orkin & Hanson, P.C.

(57) ABSTRACT

A bandage for the treatment of dermal scars, keloids, wounds or abrasions by contacting the skin of the user. The bandage includes a flexible member having a first side and a second side and further having an adhesive located on the first side. A scar treatment pad such as a layer of silicone elastomer is attached by the adhesive to the first side of the flexible member. The bandage is used by placing the first side of the flexible member in contact with the skin of the user such that the layer of silicone elastomer substantially contacts a scarred area of the skin. The adhesive removably attaches the first side of the flexible member substantially in contact with an unscarred area of the skin of the user. The layer of silicone elastomer attached to the first side of the flexible member improves the cosmetic and functional aspects of the scarred area of the skin of the user.

8 Claims, 1 Drawing Sheet

BANDAGE HAVING A SCAR TREATMENT PAD FOR SCAR MANAGEMENT AND SCAR REPAIR

CROSS-REFERENCE TO RELATED APPLICATION

This application claims the benefit of U.S. Provisional Application Serial No. 60/123,476 filed Mar. 9, 1999, entitled "Bandage Having A Silicone Sheet For Scar Management and Scar Repair".

BACKGROUND OF THE INVENTION

1. Field of the Invention

The present invention relates generally to the treatment of dermal scars, keloids, wounds and abrasions and, more particularly, to the application of silicone sheeting or silicone gel to dermal scars, keloids, wounds and abrasions for treatment thereof.

2. Description of the Prior Art

It is known in the medical field to use silicone elastomer materials (hereinafter referred to as "silicone") for the treatment of dermal scars and keloids. Silicone is known to soften scar tissue and improve the cosmetic as well as functional aspects of dermal scars and keloids. In addition, recent research indicates that certain silicone compounds promote wound healing and decrease scarring. Although the biological mechanism for the therapeutic aspects of silicone when applied to the skin is not completely understood, it is known in the art that the therapeutic benefits are derived independently of the pressure applied to the scar surface.

One prior art device that has made use of the beneficial aspects of silicone when applied to the skin is disclosed in U.S. Pat. No. 5,759,560 to Dillon. The Dillon patent discloses silicone thermoplastic sheeting for scar treatment. In particular, the Dillon patent discloses a composite structure that includes a surface layer of silicone elastomeric material applied to one side of a thermoplastic splinting material. The splinting material is shaped to fit the geometric form of the skin of the patient so that the surface layer of silicone is in uniform contact with the skin of the patient. The resulting silicone thermoplastic sheeting is in the form of a hard thermoplastic splint having the surface layer of silicone on one side and is intended to be repeatedly applied to the skin of the patient. The silicone thermoplastic sheeting material disclosed by the Dillon patent is not very user-friendly because of its hard form. The silicone thermoplastic sheeting material cannot be worn, typically, when the patient engages in ordinary daily activities because of its immobilizing nature.

Other scar management products are known to exist in the marketplace. These devices use various applications to affix silicone sheets and silicone gels to the skin of the patient to treat relatively large surface areas where scarring may be present. Typically, these devices use netting or "Ace" type elastic bandages/harnesses to hold the silicone sheet or gel in place. Consequently, these commercially available devices are not suitable for treating small cuts and are not very user-friendly. The present invention makes use of the beneficial aspects of silicone when applied to the skin but in a user-friendly form that can remain on the skin of the patient while the patient engages in ordinary daily activities. The present invention is particularly suitable for use by children and other active persons.

Consequently, the object of the present invention is to provide a user-friendly adhesive bandage for the treatment of small or localized dermal scars or keloids that can be worn by a patient while engaging in ordinary daily activities.

SUMMARY OF THE INVENTION

The present invention is an adhesive bandage for the treatment of dermal scars or keloids by contacting the skin of the patient or user. The bandage includes a flexible member having a first side and a second side and further having adhesive located on the first side. A scar treatment pad, preferably in the form of a layer of silicone elastomer such as silicone sheeting or silicone gel, or a like scar treatment substance, is attached to the first side of the flexible member. The first side of the flexible member is placed in contact with the skin of the user such that the scar treatment pad comprising the layer of silicone elastomer substantially contacts a scarred area of the skin. The adhesive on the first side of the flexible member removably attaches the first side substantially in contact with an unscarred area of the skin of the user. The flexible member preferably is slightly wider than the silicone sheet or gel scar treatment pad so as to provide an adhesive border on opposed lateral edges of the scar treatment pad. In a presently preferred embodiment of the invention, the layer of silicone elastomer is secured to a center area of the first side of the flexible member so that when the first side is in contact with the skin of the user, the first side, including the aforesaid adhesive border, is adhered to the skin around the entire perimeter of the layer of silicone elastomer, thereby preventing contaminants from entering the scar or wound area.

Preferably, the flexible member is nonocclusive and may define a plurality of ventilation holes extending from the first side to the second side of the flexible member so that the skin of the user remains exposed to the atmosphere. The flexible member may be made of polyolefin, polyurethane, nylon, polyester, vinyl or acetate taffeta or any other similar pliable material. Additionally, the flexible member may be an elastomeric woven fabric or nonwoven fabric or film. The flexible member is shaped and sized much like standard adhesive bandages which are adapted to cover healed cuts, wounds and lacerations of small to moderate size.

Preferably, the adhesive is a medical grade pressure sensitive polyisobutene (PIB) adhesive, natural rubber adhesive, acrylate and methacrylate adhesive or silicone adhesive. Preferably, the layer of silicone elastomer is a medical grade silicone.

The present invention is also directed to a method of treating dermal scars or keloids on the skin of the user using the bandage disclosed herein. The method includes the steps of providing the above described bandage and placing the first side of the flexible member in contact with the skin of the user such that the layer of silicone elastomer substantially contacts a scarred area of the skin and the first side of the flexible member substantially contacts an unscarred area of the skin of the user; and leaving the silicone elastomer in contact with the scarred area for a period of time. The adhesive removably attaches the first side of the flexible member to the skin of the user.

DETAILED DESCRIPTION OF THE PREFERRED EMBODIMENT

Figure 1:
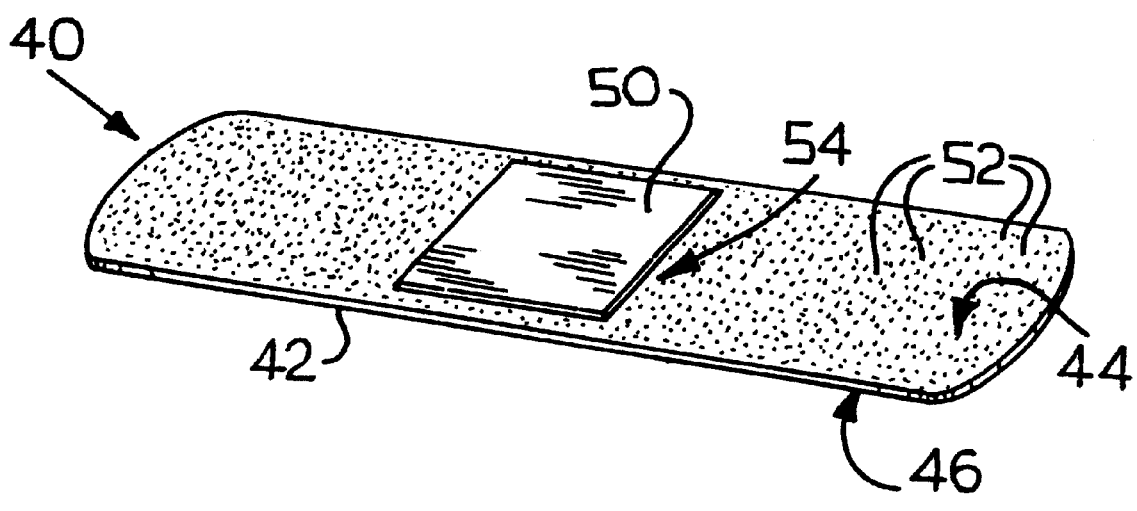
FIG. 1 is a perspective view of an adhesive bandage for treating scars and keloids of the present invention.

FIG. 1 depicts a bandage 40 made in accordance with the present invention. The bandage 40 includes an elongated flexible member 42 having a first side 44 and a second side 46. An adhesive is applied on the first side 44 of the flexible member 42. A layer of silicone elastomer forming a scar treatment pad 50 is attached by the adhesive or by some other attachment means to the first side 44 of the flexible member 42.

The flexible member 42 is preferably nonocclusive, i.e., "breathable". The flexible member 42 defines a plurality of ventilation holes 52 extending from the first side 44 to the second side 46 so that when the bandage 40 is attached to the skin of a user (not shown), the skin of the user remains exposed to the atmosphere. The flexible member 42 is substantially similar to a conventional adhesive bandage and may be made of polyolefin, polyurethane, nylon, polyester, vinyl, acetate taffeta or any other similar pliable material. Further, the flexible member 42 may be an elastomeric woven fabric, nonwoven fabric or film.

Examples of the adhesive include medical grade pressure sensitive polyisobutene (PIB) adhesives, natural rubber adhesives, acrylate and methacrylate adhesives and silicone adhesives. Preferably, the adhesive is a nonocclusive medical grade adhesive such as acrylate and methacrylate and silicone. However, any suitable nonocclusive or occlusive adhesive may be used on the first side 44 of the flexible member 42.

The layer of silicone elastomer forming the scar treatment pad 50 is a silicone sheet or a layer of silicone gel. The layer of silicone elastomer of treatment pad 50 is preferably a medical grade USP class VI silicone. The thickness of the layer of silicone elastomer may vary according to the size and shape of the bandage 40 and the size and shape of the scar or keloid to which the bandage 40 is to be applied. The scar treatment pad 50 is generally located in a central area 54 of the first side 44 of the flexible member 42. However, the scar treatment pad 50 is not limited to being centered on the first side 44 of the flexible member 42. The silicone elastomer scar treatment pad 50 preferably has a width which is slightly less than the width of the flexible member 42 to provide adhesive bearing borders 48 on opposed lateral edges of the scar treatment pad 50. This configuration is preferred, however, because the first side 44 will seal completely around a perimeter of the scar treatment pad 50 by virtue of the adhesive bearing borders 48. By sealing around the perimeter of the scar treatment pad 50, contaminants are kept out of the scar or wound area of the skin of the user. The present invention envisions that the bandage 40 is similar in size to a small Band-Aid®-like brand adhesive bandage as shown in FIG. 1, or made larger to cover large lacerations, burns and scars. Furthermore, the bandage 40 is not limited to the elongated, rectangular shape shown in the drawing and may be round, square, polygonal shaped or custom shaped to fit the size and configuration of the scar, laceration or wound. The bandage 40 is preferably packaged much like conventional adhesive bandages and includes removable strips (not shown) which cover the first side 44 and maintain cleanliness prior to use. The bandage 40 is suitable for use by children and adults.

The bandage 40 according the present invention is used by placing the first side 44 of the flexible member 42 in contact with the skin of the user such that the layer of silicone elastomer of the scar treatment pad 50 substantially contacts a scarred cut or abraded area of the skin of the user. Preferably, the adhesive on the first side 44 removably secures the first side 44 of the flexible member 42 in contact with an unscarred area of the skin of the user. The scar treatment pad 50 of the bandage 40 is left in contact with the scarred area of the skin of the user so that the layer of silicone elastomer will continuously contact the scar tissue, keloid, wound or abrasion and improve the cosmetic as well as the functional aspect of the scar, keloid, wound or abrasion. The bandage 40 is particularly useful for the management of hypertrophic scars and keloids. In the appended claims, the scar, keloid, wound or abrasion to be treated by the bandage 40 of the invention are collectively referred to as the "scarred area of the skin". The bandage 40 according to the present invention may be removed at the discretion of the user. The bandage 40 is intended to be worn until it becomes dirty, the adhesive becomes less effective in maintaining the bandage 40 in contact with the skin or the layer of silicone elastomer loses its effectiveness.

The bandage according to the present invention is further intended to include plastic, fabric or foam pressure sensitive bandages and adhesive fixing devices for attachment to the skin. Although this invention has been described with reference to a preferred embodiment, obvious modifications and alterations of the invention may be made without departing from the spirit and scope of the invention. The presently preferred material for treating scars according to the present invention is a silicone elastomer material. It will be understood, however, that the scar treatment pad 50 may comprise materials other than silicone elastomer, if such materials are medically effective in scar treatment. The scope of the present invention is defined by the appended claims and equivalents thereto.

We claim:

1. A bandage for the treatment of dermal scars, keloids, wounds and abrasions by contacting the skin of a user, comprising:

a flexible and breathable member having a first side and a second side and, further, having adhesive located on the first side; and a scar treatment pad attached to the first side of the flexible member, the scar treatment pad comprising a layer of silicone elastomer adhesively attached to a center area of the first side of the flexible member such that adhesive borders are located on lateral sides of the scar treatment pad, wherein the first side of the flexible member is adapted to be placed in contact with the skin of the user such that the scar treatment pad substantially contacts a scarred area of the skin, and such that the first side of the flexible member substantially contacts is adhesively attached to an unscarred area of the skin of the user around an entire perimeter of the scar treatment pad.

2. The bandage of claim 1, wherein the flexible member is nonocclusive.

3. The bandage of claim 1, wherein the adhesive is selected from the group consisting of medical grade pressure sensitive polyisobutene adhesives, natural rubber adhesives, acrylate and methacrylate adhesives and silicone adhesives.

4. The bandage of claim 1, wherein the layer of silicone elastomer is a medical grade silicone.

5. The bandage of claim 1, wherein the flexible member is made of a material selected from the group consisting of polyolefin, polyurethane, nylon, polyester, vinyl and acetate taffeta.

6. The bandage of claim 1, wherein the flexible member is an elastomeric woven fabric.

7. The bandage of claim 1, wherein the flexible member is an elastic nonwoven fabric.

8. A method of treating dermal scars, keloids, wounds and abrasions with a bandage, the bandage comprising:

providing a flexible and breathable member having a first side and a second side, and further having adhesive located on the first side, and a scar treatment pad comprising a layer of silicone elastomer attached by the adhesive to a center area of the first side of the flexible member such that adhesive borders are located on lateral sides of the scar treatment pad, and placing the first side of the flexible member in contact with the skin of the user such that the scar treatment pad substantially contacts a scarred area of the skin and such that the first side of the flexible member is adhesively attached to an unscarred area of the skin of the user around an entire perimeter of the scar treatment pad.

* * * * *

UNITED STATES PATENT AND TRADEMARK OFFICE
CERTIFICATE OF CORRECTION

PATENT NO. : 6,284,941 B1
DATED : September 4, 2001
INVENTOR(S) : Craig M. Cox et al.

It is certified that error appears in the above-identified patent and that said Letters Patent is hereby corrected as shown below:

Column 4,
Line 45, after "flexible member" delete "substantially contacts".

Signed and Sealed this

Twenty-sixth Day of March, 2002

*Attest:*

JAMES E. ROGAN
*Attesting Officer*     *Director of the United States Patent and Trademark Office*